United States Patent
Belzidsky

(10) Patent No.: US 7,179,242 B2
(45) Date of Patent: Feb. 20, 2007

(54) METHOD OF TREATING DEEP VEIN THROMBOSIS

(76) Inventor: Hugues C. Belzidsky, 6610 Nancy Ridge Dr., San Diego, CA (US) 92121

( * ) Notice: Subject to any disclaimer, the term of this patent is extended or adjusted under 35 U.S.C. 154(b) by 760 days.

(21) Appl. No.: 10/633,164

(22) Filed: Aug. 1, 2003

(65) Prior Publication Data

US 2005/0033392 A1 Feb. 10, 2005
US 2005/0165463 A9 Jul. 28, 2005

(51) Int. Cl.
*A61F 13/00* (2006.01)
*A61F 5/00* (2006.01)

(52) U.S. Cl. .................. 602/63; 602/20; 602/23; 602/26; 602/60; 602/62

(58) Field of Classification Search .......... 607/104, 607/108, 114; 601/149–152; 602/20, 26, 602/60, 62, 63, 75, 76, 77; 128/881, 882
See application file for complete search history.

(56) References Cited

U.S. PATENT DOCUMENTS

| | | | |
|---|---|---|---|
| 3,072,512 A | 1/1963 | Dalle | 154/46 |
| 3,373,741 A | 3/1968 | Hill et al. | 128/90 |
| 3,523,056 A | 8/1970 | Horning | 161/93 |
| 3,597,300 A | 8/1971 | Miller | 161/77 |
| 3,934,582 A | 1/1976 | Gorrie | 128/157 |
| 3,935,355 A | 1/1976 | Kuhn | 24/150 |
| 3,990,437 A | 11/1976 | Boyden, Jr. et al. | 128/90 |
| 4,019,506 A | 4/1977 | Eschmann | 128/90 |
| 4,084,586 A | 4/1978 | Hettick | 128/157 |
| 4,265,233 A | 5/1981 | Sugitachi et al. | 128/156 |
| 4,269,181 A | 5/1981 | Delannoy | 128/156 |
| 4,414,970 A | 11/1983 | Berry | 128/156 |
| 4,832,010 A | 5/1989 | Lerman | 128/165 |
| 4,841,958 A | 6/1989 | Ersfeld et al. | 128/90 |
| 4,846,164 A | 7/1989 | Martz | 128/155 |
| 4,867,150 A | 9/1989 | Gilbert | 128/155 |
| 4,888,225 A | 12/1989 | Sandvig et al. | 428/71 |
| 4,946,726 A | 8/1990 | Sandvig et al. | 428/76 |
| 5,002,047 A | 3/1991 | Sandvig et al. | 128/90 |
| 5,195,945 A | 3/1993 | Sandvig et al. | 602/8 |
| 5,203,764 A | 4/1993 | Libbey et al. | 602/5 |
| 5,455,294 A | 10/1995 | Sheng | 524/424 |
| 5,474,525 A | 12/1995 | Blott | 602/63 |
| 5,643,187 A | 7/1997 | Naestoft et al. | 602/43 |
| 6,149,690 A | 11/2000 | Belzidsky | 623/32 |
| 6,158,051 A | 12/2000 | Belzidsky | 2/22 |
| 2001/0004079 A1 | 6/2001 | Metzger | 220/495.11 |
| 2002/0115772 A1 | 8/2002 | Topolkaraev et al. | 524/401 |
| 2002/0161114 A1 | 10/2002 | Gunatillake et al. | 525/100 |
| 2002/0198433 A1 | 12/2002 | Roberts et al. | 600/9 |
| 2003/0054715 A1 | 3/2003 | Benenati et al. | 442/85 |

*Primary Examiner*—Kim M. Lewis
(74) *Attorney, Agent, or Firm*—Stephen C. Beuerle; Procopio Cory Hargreaves & Savitch

(57) ABSTRACT

A method of treating deep vein thrombosis in a limb of user includes applying a deep vein thrombosis treatment sleeve onto the limb of the user so that portions of the user's limb extend from opposite open ends of the deep vein thrombosis treatment sleeve; allowing the deep vein thrombosis treatment sleeve to conform to the limb and adhere to the limb over the area of the user's limb where the deep vein thrombosis resides through negligible compression suction adhesion; heating up the deep vein thrombosis treatment sleeve with a user's body heat so that the user barely notices the deep vein thrombosis treatment sleeve on the user's limb; and treating the deep vein thrombosis with the deep vein thrombosis treatment sleeve on the limb of the user over the area of the user's limb where the deep vein thrombosis resides. The treatment sleeve may also be used for treating a ligament or muscle injury in a joint of a user.

17 Claims, 3 Drawing Sheets

METHOD OF TREATING DEEP VEIN THROMBOSIS

FIELD OF THE INVENTION

The present invention relates, in general, to therapeutic medical devices and methods, and, in particular, to devices and methods for treating deep vein thrombosis.

BACKGROUND OF THE INVENTION

Deep vein thrombosis (DVT) and pulmonary embolism (PE) constitute major health problems in the United States. It has been estimated that 300,000 to 600,000 hospitalizations a year are attributable to DVT and PE conditions. Venous thromboembolism is also a significant risk in surgical patient populations where preoperative, operative and postoperative immobilization with concomitant loss of venous pump function causes blood stasis.

The use of prophylactic antithrombotic drugs for preventing DVT are known to the art. However, the efficacy of prophylactic administration of anticoagulants and antiplatelet agents has been disputed, and is certainly not absolute. An alternative approach, attractive because of its freedom from hemorrhagic side effects, is the use of specially fitted compression stockings designed to treat or help prevent blood clots from developing in deep leg veins. These stockings are available from a medical supply store with a doctor's prescription or over the counter at some pharmacies. There are generally two types of compression stockings used for deep leg vein thrombosis. The type recommended will usually be based upon one of two treatment goals: 1) to relieve symptoms associated with existing deep leg vein thrombosis, especially swelling and pain, and prevent post-thrombotic syndrome. This type of stocking may also help prevent additional clots from forming, although this is not its primary function. Compression stockings for existing deep leg vein thrombosis are expensive, usually around $150 per pair. 2) To reduce the risk of developing deep leg vein thrombosis in people who are at high risk. This kind of compression stocking is less expensive than those used to help treat existing deep leg vein thrombosis.

Compression stockings are tight at the feet with a gradually looser fit on the leg (graduated compression). They are as thick as two pairs of regular panty hose and cover the leg from the arch of your foot to just below or above your knee. Compression stockings are also available as a panty hose or trouser socks.

Compression stockings have disadvantages. The compressive nature of the stockings make them uncomfortable to wear, especially when worn all day. They are hot and may be difficult to put on, especially for older adults, overweight people, and people with arthritis. Also, many medical professionals do not believe compression stockings are useful to treat deep leg vein thrombosis.

SUMMARY OF THE INVENTION

Accordingly, an aspect of the invention involves a deep vein thrombosis treatment sleeve and method of treating deep vein thrombosis in a limb of a user where a deep vein thrombosis treatment sleeve made of materials such as, but not limited to, urethane, polyurethane, or polyether-based aromatic polyurethane is applied to and maintained in position on a limb of a user suffering from deep vein thrombosis over the area where the deep vein thrombosis exists through negligible compressive suction adhesion to treat deep vein thrombosis without the discomfort suffered by compression stocking users.

Another aspect of the invention involves a method of treating deep vein thrombosis in a limb of user. The method includes providing a deep vein thrombosis treatment sleeve having a generally tubular configuration with at least one open end in use and configured to apply negligible compressive engagement to the limb of the user disposed thereon; applying the deep vein thrombosis treatment sleeve onto the limb of the user over the area of the user's limb where the deep vein thrombosis resides and a portion of the user's limb extends from at least one open end of the deep vein thrombosis treatment sleeve; allowing the deep vein thrombosis treatment sleeve to conform to the limb and adhere to the limb over the area of the user's limb where the deep vein thrombosis resides through negligible compression suction adhesion; heating up the deep vein thrombosis treatment sleeve with the body heat of the user until the deep vein thrombosis treatment sleeve reaches the body temperature of the limb the deep vein thrombosis treatment sleeve is applied to so that the user barely notices the deep vein thrombosis treatment sleeve on the user's limb; and treating the deep vein thrombosis with the deep vein thrombosis treatment sleeve on the limb of the user over the area of the user's limb where the deep vein thrombosis resides.

A further aspect of the invention involves a method of treating a ligament or muscle injury in a joint of a user. The method includes providing a treatment sleeve having a generally tubular configuration with at least one open end in use and configured to apply negligible compressive engagement to the joint of the user disposed thereon; applying the treatment sleeve onto the joint of the user where the ligament or muscle injury resides, the joint being at least one of a knee, an ankle, an elbow, and a wrist of the user; allowing the treatment sleeve to conform to the joint and adhere to the joint over the area of the ligament or muscle injury through negligible compression suction adhesion; heating up the treatment sleeve with the body heat of the user until the treatment sleeve reaches the body temperature of the joint the treatment sleeve is applied to so that the user barely notices the treatment sleeve on the user's joint; and treating the ligament or muscle injury in the joint with the treatment sleeve on the joint of the user over the area of the user's joint where the ligament or muscle injury resides.

Further objects and advantages will be apparent to those skilled in the art after a review of the drawings and the detailed description of the preferred embodiments set forth below.

DETAILED DESCRIPTION OF PREFERRED EMBODIMENTS

Figure 1:
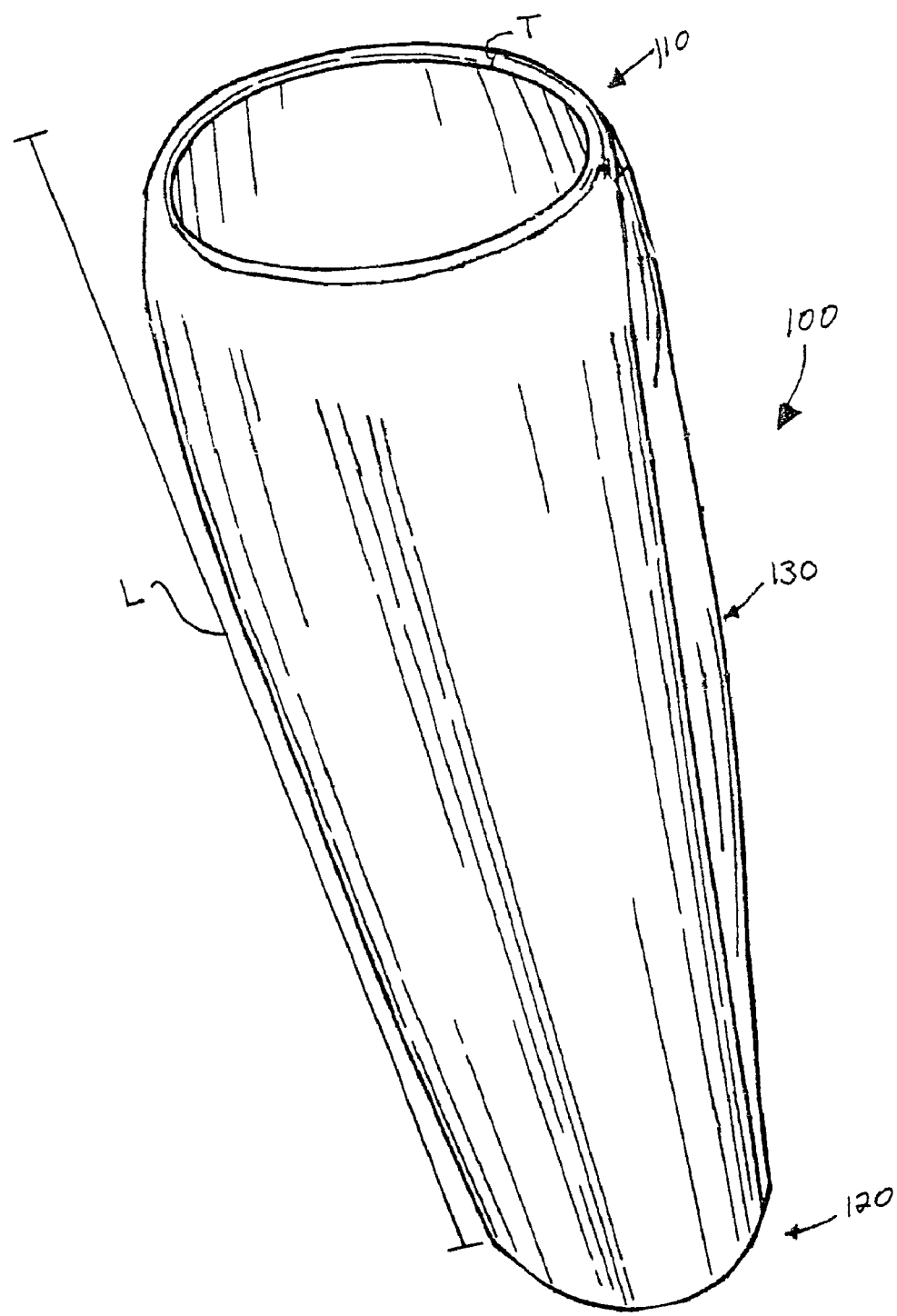
FIG. 1 is a perspective view of an embodiment of a treatment sleeve that may be used for treating deep vein thrombosis and the associated pain.

With reference to FIG. 1, an embodiment of a treatment sleeve 100 and associated method for treating deep vein thrombosis and the associated pain in a user's leg, arm, or pelvis will now be described. Although the treatment sleeve 100 will initially be described for the treatment of deep vein thrombosis, the treatment sleeve 100 may be used to treat other complications such as, but not limited to, sports injuries, ligament sprains or tears, muscle strains or tears, pain areas, carpal tunnel syndrome, joint injuries in the legs and other areas of the body, and other related injuries.

Figure 2:
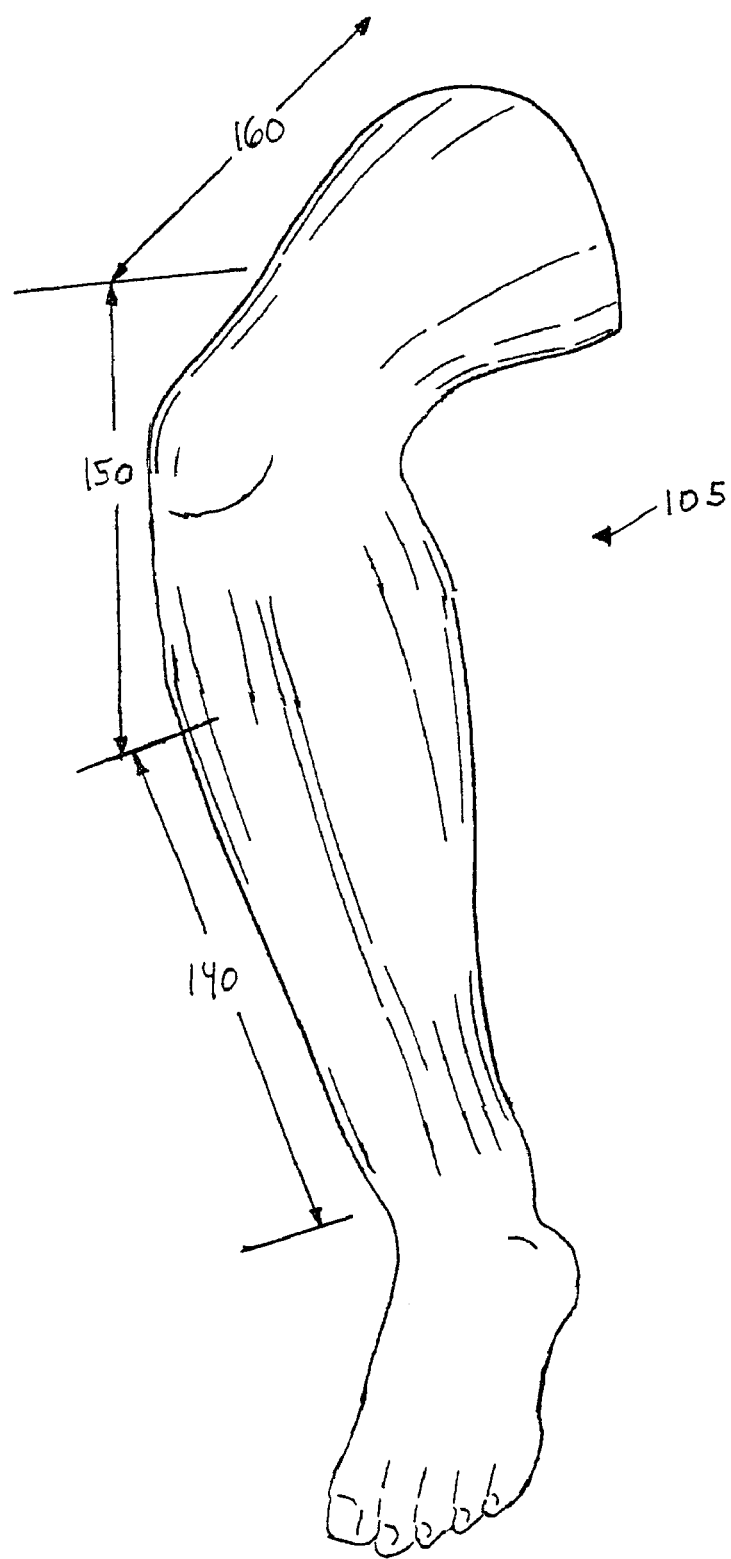
FIG. 2 is a perspective view of a leg of a user and illustrates areas of the leg where the treatment sleeve may be applied for treating deep vein thrombosis or an injury area and the associated pain.
Figure 3:
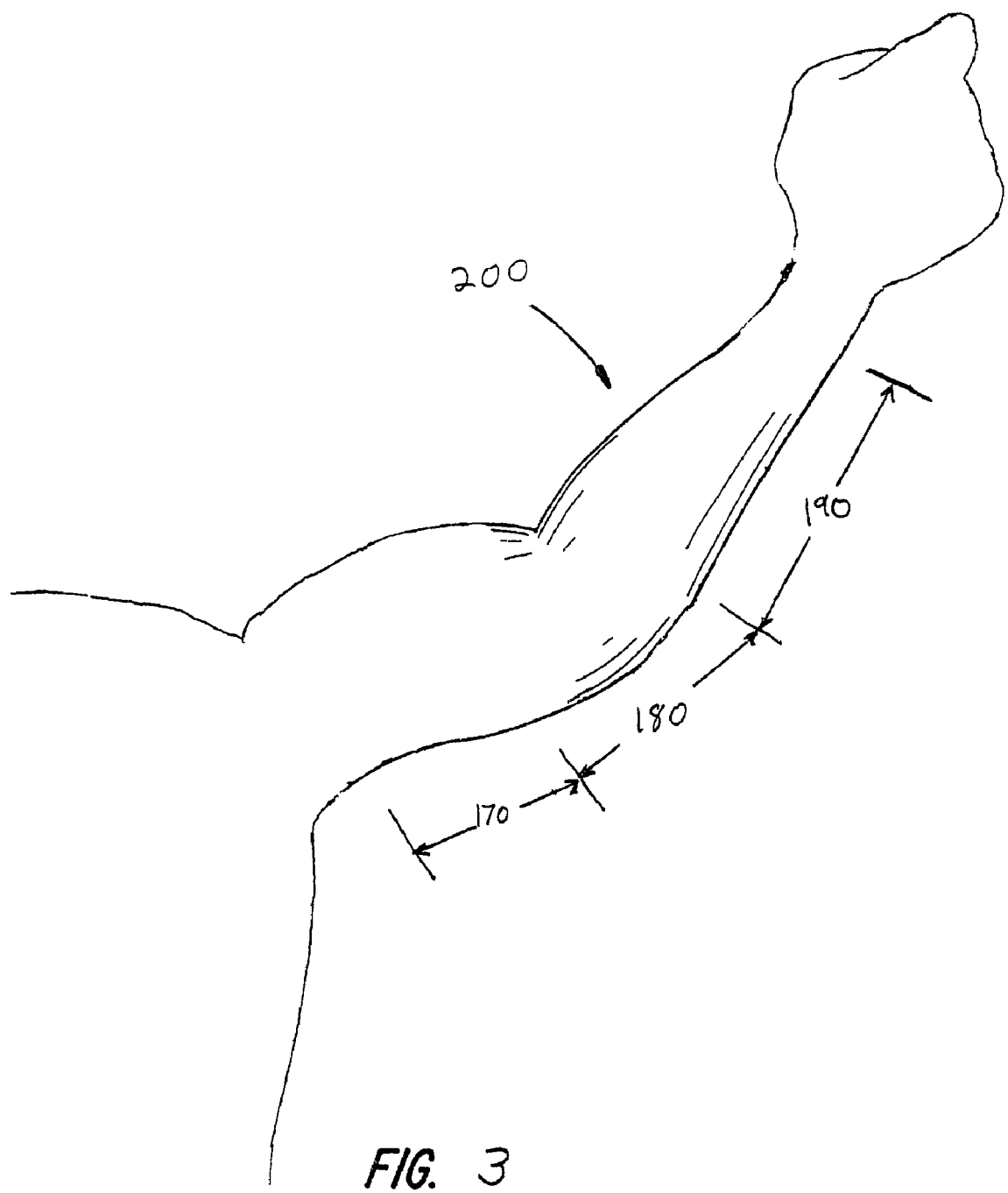
FIG. 3 is a rear elevational view of an arm of a user and illustrates injury areas of the arm where the treatment sleeve may be applied for treating deep vein thrombosis or an injury area and the associated pain.

In the embodiment shown, the treatment sleeve 100 has a generally tubular shape, and, more specifically, a generally truncated conical shape sized and configured to snugly conform to the shape of a lower leg 105 (FIG. 2) or an arm 200 (FIG. 3) of a wearer. The treatment sleeve 100 has a larger diameter circular open end 110 and a smaller diameter circular open end 120 connected by a generally conical main body portion 130 of a uniform elasticity. The treatment sleeve 100 has a thickness T that preferably ranges between 1.5 mm–6 mm and a length L that preferably ranges from 12 cm (e.g., a narrow band) to the distance between the end of a user's foot and the ischium; however, in alternative embodiments, the treatment sleeve 100 has a thickness T and/or length L outside of this range.

The treatment sleeve 100 is preferably injection molded and made of a resiliently stretchable non-compressive material that naturally adheres to the skin of the wearer with negligible compression on the skin of the wearer. As used herein, "negligible compression" means at body temperature the treatment sleeve 100 does not interfere with any blood flow of the user. The material of the treatment sleeve 100 is advantageously soft at body temperature, conforms and adheres to the shape of the body part thereunder through non-compressive suction adhesion to maintain the sleeve in position upon the body part with negligible compression and without restricting blood flow and shifting of the treatment sleeve 100 during movement or physical activity. Exemplary materials that may be used for the treatment sleeve 100 are urethane or polyurethane. In a preferred embodiment, the sleeve 100 is made of a polyether-based aromatic polyurethane material. The urethane or polyurethane material has excellent memory which enables the sleeve 100 to return to its original shape or the shape of the body part hereunder while applying negligible compressive forces on the user's skin after stretching. Although the treatment sleeve 100 is described as preferably being made of polyurethane or urethane, in alternative embodiments, the treatment sleeve 100 may be made of an elastic silicone or another material that is elastic, provides negligible compression at body temperature, and adheres to the skin of the user naturally. The material of the sleeve 100 may be optionally reinforced with a cloth reinforcement that does not interfere with the elasticity of the sleeve 100.

When the treatment sleeve 100 is applied over a joint (e.g., knee, elbow, wrist, ankle) and is at body temperature, the sleeve 100 does not interfere with flexion of the joint.

Although the treatment sleeve 100 is shown as having a generally tubular construction with two open ends 110, 120, in alternative embodiments, the treatment sleeve 100 may have an open end 110 and a closed end 120 (e.g., the closed end may be snug around the user's toes in a foot application), the treatment sleeve 100 may have an open end 110 and a closed end 120 with substantially the same size or diameter, or the treatment sleeve 100 may have other configurations or the treatment sleeve 100 may be made of a flat piece or sheet of material that is wrapped circumferentially around the user's leg 105 or other body part. For example, in such an embodiment, opposite end portions of the flat piece of material may include respective hook fasteners and loop fasteners (e.g., Velcro®) to connect the opposite end portions for circumferential attachment of the treatment sleeve 100 around the user's leg 105 or other body part.

To treat deep leg vein thrombosis, the treatment sleeve 100 is applied to the user's leg 105 over the location of the deep leg vein thrombosis. The user's foot is inserted through the larger diameter circular open end 110, fed through the generally conical main body portion 130, and inserted out through the smaller diameter circular open end 120, similar to feeding one's leg through the leg of one's pants when putting on one's pants. The treatment sleeve 100 is then pulled up the user's leg 105 to the location of the deep vein thrombosis. It should be noted that when applying the treatment sleeve to the user's leg 105, the treatment sleeve 100 is elastically stretched. When the treatment sleeve is in position over the location of the deep vein thrombosis, the memory of the elastic treatment sleeve 100 enables the sleeve 100 to conform to the shape of the user's leg 105. The user's body heats the treatment sleeve 100 up to the temperature of the user's body in approximately 10–15 minutes. Once the treatment sleeve 100 is at body temperature, the treatment sleeve 100 is advantageously soft, conforming and adhering to the shape of the user's leg thereunder through non-compressive suction adhesion to maintain the sleeve 100 in position upon the user's leg with negligible compression and without restricting blood flow in the leg 105. In this position, the treatment sleeve 100 creates a sealed environment around the target deep vein thrombosis or pain area without an adhesive such as glue and with negligible compression. In this condition, the treatment sleeve 100 also takes on the feel of another layer of skin to the user so that the user barely notices or does not notice the treatment sleeve 100. Application of the treatment sleeve 100 causes the pain, swelling, and other symptoms from deep vein thrombosis in the leg 105 to subside. Because of the negligible compression of the treatment sleeve 100 and skin-like feel that the treatment sleeve 100 takes on after the body warms it to body temperature, the treatment sleeve 100 can be worn for long periods of time without discomfort. The user may remove the treatment sleeve 100 from the leg 105, in an opposite manner to that described above for applying the treatment sleeve 100 to the leg 105, similar to removing one's pant leg of one's pants when taking off one's pants. It has been determined that the user continues not to feel pain from deep vein thrombosis or the pain is minimized for a period of time after the treatment sleeve 100 is removed from the user's leg 105. Further, the period of time that the user does not feel pain, swelling or other symptoms from deep vein thrombosis after removing the treatment sleeve 100 increases the longer the treatment sleeve 100 is applied to the user's leg 105.

The treatment sleeve 100 may be applied to one or more of a lower leg area 140, a knee area 150, an upper leg area 160, a bicep area 170, an elbow area 180, and a forearm/wrist area 190 for treating deep vein thrombosis or for treating other complications. Although the treatment sleeve 100 has been described for the treatment of deep vein thrombosis, the treatment sleeve 100 may be used to treat other complications such as, but not limited to, sports injuries, ligament sprains or tears, muscle strains or tears, pain areas, carpal tunnel syndrome, and joint injuries in the legs and other areas of the body. Similar to that described above for treating deep vein thrombosis, it has been determined that the user continues not to feel pain from the sports injury, ligament sprain, etc. or the pain is minimized for a period of time after the treatment sleeve 100 is removed from the user's limb. Further, the period of time that the user does not-feel pain or other symptoms from the sports injury, ligament sprain, etc. after removing the treatment sleeve 100 increases the longer the treatment sleeve 100 is applied to the user's limb.

It will be readily apparent to those skilled in the art that still further changes and modifications in the actual concepts described herein can readily be made without departing from the spirit and scope of the invention as defined by the following claims.

What is claimed is:

1. A method of treating deep vein thrombosis in a limb of a user, comprising:
   providing a deep vein thrombosis treatment sleeve having a generally tubular configuration with at least one open end in use and configured to apply negligible compressive engagement to the limb of the user disposed thereon;
   applying the deep vein thrombosis treatment sleeve onto the limb of the user over the area of the user's limb where the deep vein thrombosis resides and a portion of the user's limb extends from at least one open end of the deep vein thrombosis treatment sleeve;
   allowing the deep vein thrombosis treatment sleeve to conform to the limb and adhere to the limb over the area of the user's limb where the deep vein thrombosis resides through negligible compression suction adhesion;
   heating up the deep vein thrombosis treatment sleeve with the body heat of the user until the deep vein thrombosis treatment sleeve reaches the body temperature of the limb, the deep vein thrombosis treatment sleeve is applied to so that the user barely notices the deep vein thrombosis treatment sleeve on the user's limb;
   treating the deep vein thrombosis with the deep vein thrombosis treatment sleeve on the limb of the user over the area of the user's limb where the deep vein thrombosis resides.

2. The method of claim 1, wherein the deep vein thrombosis treatment sleeve is made of urethane.

3. The method of claim 1, wherein the deep vein thrombosis treatment sleeve is made of polyurethane.

4. The method of claim 1, wherein the deep vein thrombosis treatment sleeve is made of polyether-based aromatic polyurethane.

5. The method of claim 1, wherein the deep vein thrombosis treatment sleeve is made of an elastic silicone material with negligible compression at body temperature while adhering naturally to the user's skin.

6. The method of claim 1, wherein the deep vein thrombosis treatment sleeve is made of an elastic silicone material with negligible compression at body temperature while adhering naturally to the user's skin.

7. The method of claim 1, wherein the deep vein thrombosis treatment sleeve is provided in a flat sheet of material prior to application onto the limb, and is wrapped around the limb.

8. The method of claim 1, wherein the deep vein thrombosis treatment sleeve includes opposite open ends.

9. The method of claim 8, wherein one of the opposite open ends of the deep vein thrombosis treatment sleeve is larger than the other.

10. The method of claim 8, wherein the opposite open ends are substantially the same size.

11. The method of claim 1, wherein the limb is a leg.

12. The method of claim 1, wherein the limb is an arm.

13. The method of claim 1, wherein the limb includes at least one joint that the deep vein thrombosis treatment sleeve is applied to, and at body temperature the deep vein thrombosis treatment sleeve does not interfere with flexion of the at least one joint.

14. The method of claim 1, wherein the deep vein thrombosis treatment sleeve has a truncated conical configuration.

15. The method of claim 1, wherein the deep vein thrombosis treatment sleeve is reinforced with a cloth reinforcement.

16. The method of claim 1, further including removing the deep vein thrombosis treatment sleeve, and symptoms of the deep vein thrombosis not returning for a period of time after the removing the deep vein thrombosis treatment sleeve.

17. The method of claim 16, wherein the period of time that the symptoms of the deep vein thrombosis do not return after removing the deep vein thrombosis treatment sleeve increases with increases in the amount of time that the deep vein thrombosis treatment sleeve is applied, and the method further includes increasing the amount of time that the deep vein thrombosis treatment sleeve is applied to the limb before removing the deep vein thrombosis treatment sleeve to increase the period of time that the symptoms of the deep vein thrombosis do not return after removing the deep vein thrombosis treatment sleeve.

* * * * *